United States Patent
Rosenberg

(10) Patent No.: US 7,699,810 B2
(45) Date of Patent: Apr. 20, 2010

(54) MEANS FOR RETAINING TRANSCUTANEOUS CATHETERS AND NEEDLES IN PLACE

(75) Inventor: Lior Rosenberg, Omer (IL)

(73) Assignee: L.R.R. & D Ltd., Omer (IL)

( * ) Notice: Subject to any disclaimer, the term of this patent is extended or adjusted under 35 U.S.C. 154(b) by 984 days.

(21) Appl. No.: 10/470,232

(22) PCT Filed: Jan. 24, 2002

(86) PCT No.: PCT/IL02/00073

§ 371 (c)(1), (2), (4) Date: Jan. 30, 2004

(87) PCT Pub. No.: WO02/058774

PCT Pub. Date: Aug. 1, 2002

(65) Prior Publication Data

US 2004/0112510 A1   Jun. 17, 2004

(30) Foreign Application Priority Data

Jan. 25, 2001   (IL) .................................... 141117

(51) Int. Cl.
   *A61M 5/32*   (2006.01)
(52) U.S. Cl. .................................... 604/180
(58) Field of Classification Search ............ 604/164.01, 604/174, 179, 180; 602/52, 54
   See application file for complete search history.

(56) References Cited

U.S. PATENT DOCUMENTS

| | | | | |
|---|---|---|---|---|
| 3,670,729 A | * | 6/1972 | Bennett et al. | 604/500 |
| 3,720,210 A | * | 3/1973 | Diettrich | 604/533 |
| 4,586,974 A | | 5/1986 | Nystrom et al. | |
| 5,352,200 A | * | 10/1994 | Hammett et al. | 604/110 |

FOREIGN PATENT DOCUMENTS

| | | |
|---|---|---|
| EP | 09188341 | 7/1997 |
| WO | WO 01/12253 | 2/2001 |
| WO | WO 01/82817 | 11/2001 |

* cited by examiner

*Primary Examiner*—Nicholas D Lucchesi
*Assistant Examiner*—Theodore J Stigell
(74) *Attorney, Agent, or Firm*—Reed Smith LLP

(57) ABSTRACT

Method of holding in place a transcutaneous implant by applying an adhesive in liquid form to the implant and the area of the patient's skin about the needle and allowing the adhesive to set. The implant is constituted by an infusion needle, a catheter or any transcutaneous implant. Whenever the adhesive is in liquid form, it has such a surface tension that it will flow along the implant and the skin to reach a terminal point, which is the point at which the implant is inserted. The adhesive is applied in liquid form and flows along the implant and the skin to reach the point at which the implant is inserted, and then allowed to set to hold the implant in place.

7 Claims, 1 Drawing Sheet

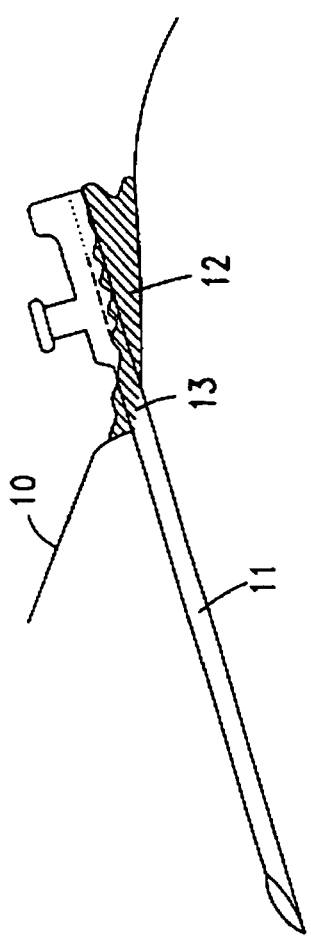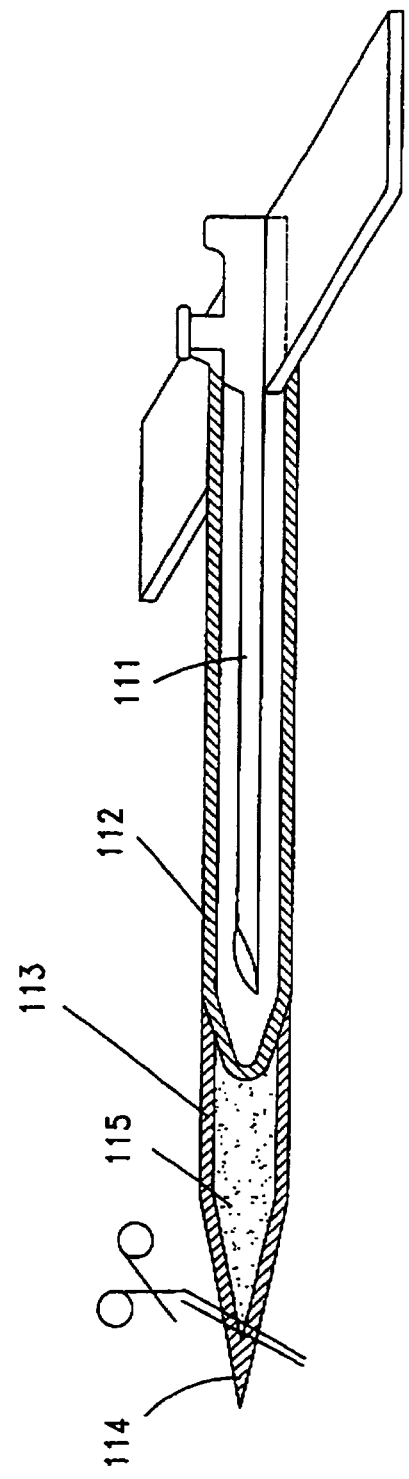

MEANS FOR RETAINING TRANSCUTANEOUS CATHETERS AND NEEDLES IN PLACE

FIELD OF THE INVENTION

The invention relates to means for holding infusion needles and catheters in place after they have been applied and inserted into a person's vessels. More specifically, it relates to a novel use of known chemical compounds for holding transcutaneous implants in place.

BACKGROUND OF THE INVENTION

Transcutaneous needles and catheters, once inserted into a patient's organs or vessels, must be kept in place for considerable lengths of time, sometimes for days consecutively. In present practice, this is done by suturing the implant to the skin or applying a tape, or like adhesive strip or film, to the skin on both sides of the needle. The tape or adhesive strip is passed over the needle and keeps it tight against the skin. This way of holding these transcutaneous implants in place is awkward and not effective and sometimes very disturbing to the patient, particularly if it used for many hours or even days consecutively. In many cases, it may actually be painful to the patient or even cause irritation and ulceration and not be effective in stabilizing the implant and invasive stitching of the implant to the skin may be needed.

Additionally, the opening created by the insertion of the transcutaneous implant such as a needle into the patient's skin may permit the entrance of microbes (contamination) and infection in general. The adhesive tape or film may create a moist, occlusive microenvironment that promotes the onset and propagation of such an infection.

It should be understood that while reference is made to transcutaneous needles, in particular to infusion needles, and while this is the most typical application of the invention, the invention can be applied to holding in place needles, catheters, tubes, wires, etc., that are transcutaneous, e.g. infusion needles, catheters, tubes, soprapubic catheters, electrical leads (such as pacemaker), spinal and gastrotomy catheters and tubes, etc., and in general any implant, and this extension of the invention should be understood as implicitly repeated every time that a reference is made to the use of the invention for holding transcutaneous implants or infusion needles in place.

It is therefore a purpose of this invention to provide means for holding an infusion needle in place that are more efficient, comfortable and easier to apply than those known in the art.

It is another purpose of this invention to provide such means that seal the opening created by the insertion of the needle into the patient's skin and prevents infection.

It is a further purpose of this invention to provide a novel use for known chemical compounds.

It is a still further purpose of the invention to provide a novel use for known chemical compounds which consists in applying them to retain infusion needles in place in a patient's veins and sealing the opening created by the insertion of the needle.

It is a still further purpose of this invention to provide means for holding infusion needles in place that consist in the use of chemical substances which are available on the market and intended for other uses.

It is a still further purpose of this invention to provide means for effectively holding infusion needles in place that is completely painless and non-irritating to the patient.

SUMMARY OF THE INVENTION

The invention provides a novel means of holding in place a transcutaneous implant in general, and particularly an infusion needle or catheter, which comprises applying an adhesive in liquid form to the implant and the area of the patient's skin about the needle and allowing the adhesive to set, firmly to hold the implant into place. From now on, the invention will be described, for brevity's sake, with reference to a transcutaneous implant constituted by an infusion needle.

In a preferred form of the invention, the adhesive, when in liquid form, has such a surface tension that it may be applied at one point of a body and will flow along said body to reach a terminal point or a limited area about and/or beyond a terminal point. The terminal point will depend on the configuration of the said body. For example, the liquid adhesive may be applied at the end of a needle or at intermediate point thereof and it will flow along the needle at the interface with the skin, to reach the point at which it is inserted, which is, in this case, the terminal point. Thereafter the adhesive sets to become a solid seal about the needle and the skin. Typically, the adhesive is a monomeric compound and sets by polymerization.

In any case, the adhesive forms a seal which prevents the propagation of microbes and in general of contaminating and polluting material through the stab-wound opening of the skin produced by the insertion of the needle.

The invention therefore provides a novel use for adhesives having the aforesaid properties, which novel use is to hold an implant into place and prevent infections that might be caused or facilitated by the presence of the implant or the dressings that are designed to hold it in place.

A preferred class of adhesives that can be used according to the invention is that of the esters of 2-cyanoacrylic acid, which are used in surgery to hold closed easily approximated skin edges of wounds from surgical incisions and trauma-induced lacerations One such ester is the octyl ester, the use of which is most preferred according to the invention. Another such ester is the isobutyl ester.

Accordingly, the invention provides a novel use for chemical substances which are esters of 2-cyanoacrylic acid, which novel use is to hold an infusion needle in place. The ester can be applied in liquid form at one end of the needle outside the skin or at intermediate portion of the needle, and/or to the adjacent area of the skin, and will flow, due to surface tension, along the needle and/or the skin all the way to the point in which the needle penetrates through the skin and around said point. The ester will then polymerize in a very short time, generally in the order of seconds, and form a solid glue and a seal binding the needle to the skin and sealing the space around the point of penetration of the needle. Nothing is required to cause the polymerization of said esters of 2-cyanoacrylic acid. Said polymerization generally requires the presence of water, but the skin always provides the small amount of moisture required.

When the needle is to be removed, it may be pulled out and the polymerized adhesive will come off with it. However, it may be desirable to apply some oily material (such as ointments or creams, to loosen the bond between the glue and the skin.

2-octyl cyanoacrylate is available on the market and is particularly manufactured by Closure Medical Company and sold by Ethicon, Inc., of Summerhill, N.J., a Johnson & Johnson Company, under the name Dermabond™. It is actually packaged and sold in glass ampoules, to prevent it from polymerizing before its use. As presently available on the market, the glass ampoule that containing liquid 2-octyl cyanoacrylate, is contained within a plastic vial with attached applicator tip. Once the glass ampoule has been crushed, the liquid can be applied through the applicator. This, however, is not essential to the invention. It is sufficient that 2-octyl cyanoacrylate be provided in a closed container, so as to prevent its premature polymerization, and that the closed container have means for discharging the liquid it contains out and directing it onto the needle to be retained and the adjacent portions of the skin. For instance, a certain quantity of 2-octyl cyanoacrylate could be contained in a syringe, the outlet of which is fully closed by a cap. At the moment of the application, the cap could be removed and the liquid 2-octyl cyanoacrylate could be forced out of the syringe either through its outlet, left free by the removed cap, or through a discardable, short needle to be applied to said syringe outlet. Another possibility is to use a modified needle-hub that is provided with the implant and will contain the required amount of liquid adhesive. After removing the protection hub, the implant is inserted and the tip of the hub is cut to allow the liquid to flow (as is done with the Histoacryl tube). Persons skilled in the art can devise many means for storing the 2-octyl cyanoacrylate without allowing it to polymerize and for applying it at the moment at which it is desired to hold in place an infusion needle or the like. Persons skilled in the art can devise many ways and means to combine the adhesive liquid container with the implant package in order to make its use easier.

2-isobutyl cyanoacrylate is available on the market under the trade name Histoacryl™. It may be obtained, for instance, from B. Braun Surgical AG in Switzerland. It comes in a long neck plastic tube. Once the tip of the neck is cut the tubular long neck is used to deposit the glue at its action site.

However, it should be understood that, while references have been made to cyanoacrylic esters, any fast setting, biocompatible adhesive with high enough surface tension may be used for holding a transcutaneous implant in place.

The implant may be provided with a connector (Luer type) with some flat protrusions (as in the currently available I.V. infusion needles and catheters) to increase the surface that is glued to the skin.

BRIEF DESCRIPTION OF THE DRAWINGS

In the drawings:

FIG. 1 illustrates in schematic perspective view an infusion needle inserted into a patient's vein and held in place according to an embodiment of the invention; and FIG. 2 illustrates the modified protective-hub with its glue container.

DETAILED DESCRIPTION OF PREFERRED EMBODIMENTS

In FIG. 1, numeral 10 schematically indicates the skin of a patient and numeral 11 indicates an infusion needle which has been inserted into the patient's body. Although the needle is assumed to be an infusion needle, the vein into which it is inserted is not shown. The shaded area 12 indicates the adhesive which has been applied at the outer end of the needle and has flown by surface tension to fill the area 12 and has polymerized in place. It is seen that the adhesive not only connects the needle to the skin, but also provides a seal at the point generally indicated at 13 at which the needle passes through the skin.

In FIG. 2 numeral 111 schematically indicates the needle or any transcutaneous implant. Numeral 112 indicates a protective hub similar to protective hubs known in the art. Numeral 113 indicates the glue tube-like container attached to the hub's end. The container 113 is filled with the glue 115 and ends with an elongated tip that may be cut and used to spread the glue.

While embodiments of the invention have been described by way of illustration, it will be apparent that the invention may be carried out with various modifications and adaptations without departing from its spirit or exceeding the scope of the claims.

The invention claimed is:

1. A medical assembly comprising:
a transcutaneous implant;
a protective hub package in which an the transcutaneous implant is removably retained, said package having a proximal end and a distal end; and
a tube-like container containing a biocompatible adhesive in liquid form attached to said distal end of said hub package;
wherein said hub package is configured to permit removal of said implant therefrom at said proximal end exclusively, thereby preventing penetration of said implant within said container and application of said adhesive onto said implant while said implant is retained within said hub package,
said adhesive being dischargeable from said container to the implant and to a selected area of the patient's skin about the implant following removal of said implant from said hub package, whereby to become a solid seal, to secure said implant to the selected skin area, and to inhibit contamination and propagation of infections from surrounding skin into a transcutaneous tract caused by insertion of said implant within said skin area.

2. The medical assembly according to claim 1, wherein the tube-like container is formed with a tip at a distal end thereof, said tip severable from the container and adapted to apply the discharged adhesive onto the implant.

3. The medical assembly according to claim 1, wherein the implant is selected from the group of infusion needles, catheters, tubes, wires, and electrical leads.

4. The medical assembly according to claim 1, wherein the solid seal is constituted by polymerized acrylic monomers.

5. The medical assembly according to claim 4, wherein the solid seal is constituted by polymerized esters of 2-cyanoacrylic acid.

6. The medical assembly according to claim 1, which is elongated and finger graspable following removal of the implant from the hub package, to facilitate discharge of the adhesive from the container to the implant and to the selected area of the patient's skin about the implant.

7. The medical assembly according to claim 1, wherein the implant has a proximal end wider than the proximal end of the hub package, to prevent displacement of the implant to the distal end of the hub package.

* * * * *